United States Patent [19]
Habuchi et al.

[11] Patent Number: 5,849,722
[45] Date of Patent: Dec. 15, 1998

[54] OLIGOSACCHARIDE HAVING AFFINITY FOR FIBROBLAST GROWTH FACTOR AND PROCESS FOR PRODUCING SAME

[75] Inventors: Hiroko Habuchi; Sakaru Suzuki; Koji Kimata, all of Aichi, Japan

[73] Assignee: Seikagaku Kogyo Kabushiki Kaisha, Tokyo, Japan

[21] Appl. No.: 471,174

[22] Filed: Jun. 6, 1995

Related U.S. Application Data

[63] Continuation of Ser. No. 868,843, Apr. 16, 1992, abandoned.

[30] Foreign Application Priority Data

Apr. 16, 1991 [JP] Japan .................................. 3-110905

[51] Int. Cl.$^6$ .......................... A61K 31/725; C08B 37/10
[52] U.S. Cl. ................. 514/56; 514/12; 514/21; 514/54; 536/21; 536/53; 536/55.3; 536/123; 530/399; 530/412; 530/413; 435/101
[58] Field of Search .................. 514/12, 21, 54, 514/56; 536/21, 53, 55.3, 123; 530/399, 412, 413; 435/101

[56] References Cited

U.S. PATENT DOCUMENTS

| | | | |
|---|---|---|---|
| 4,788,307 | 11/1988 | Lormeau et al. | 536/21 |
| 5,034,520 | 7/1991 | Lormeau et al. | 536/127 |
| 5,100,668 | 3/1992 | Edelman et al. | 530/399 |
| 5,126,323 | 6/1992 | Rogers et al. | 514/12 |
| 5,175,147 | 12/1992 | Folkman et al. | 514/21 |

FOREIGN PATENT DOCUMENTS

| | | |
|---|---|---|
| 0014184 | 8/1980 | European Pat. Off. . |
| 0287477 | 10/1988 | European Pat. Off. . |
| 0394971 | 10/1990 | European Pat. Off. . |
| 240399 | 2/1990 | Japan . |
| 9001501 | 2/1990 | WIPO . |

OTHER PUBLICATIONS

Turnbull et al; The Biochemical Journal 251:597–608 (1988). Month Not Available.
Ripellino et al; Journal of Neurochemistry 52: 807–812 (1989). Month Not Available.
Bashkin et al; Biochemistry 28:1737–1743 (1989). Month Not Available.
Linhardt et al; Biochemistry 29(10):2011–2017 (Mar. 1990).
Nader et al; Journal of Biological Chemistry 265(28):16807–16813 (Oct. 1990).
Sakaguchi et al; Journal of Biological Chemistry 266(11):7270–7278 (Apr. 1991).
Ornitz et al; Molecular and Cellular Biology 12:240–247 (Jan. 1992).
Turnbull et al; Journal of Biological Chemistry 267(15):10337–10341 (May 1992).
Habuchi et al; Biochemical Journal 285:805–813 (Aug. 1992).

*Primary Examiner*—Kathleen K. Fonda
*Attorney, Agent, or Firm*—Sughrue, Mion, Zinn, Macpeak & Seas, PLLC

[57] ABSTRACT

An oligosaccharide having an affinity for fibroblast growth factor, which is composed of 8 to 18 monosaccharide residues, wherein a principal disaccharide unit comprising L-iduronic acid 2-sulfate and N-sulfo-D-glucosamine and a process for producing the oligosaccharide comprising digesting heparan sulfate.

8 Claims, 4 Drawing Sheets

OLIGOSACCHARIDE HAVING AFFINITY FOR FIBROBLAST GROWTH FACTOR AND PROCESS FOR PRODUCING SAME

This is a continuation of application Ser. No. 07/868,843, filed Apr. 16, 1992, now abandoned.

FIELD OF THE INVENTION

This invention relates to an oligosaccharide having an affinity for fibroblast growth factor and to a process for producing same. More particularly, this invention relates to an oligosaccharide which has an affinity for fibroblast growth factor but does not react with antithrombin III, heparin cofactor II, platelet factor 4 and the like, and to a process for producing same.

BACKGROUND OF THE INVENTION

Basic fibroblast growth factor (hereinafter referred to as "bFGF") is a protein of 146 amino acid residues which strongly enhances growth of markedly broad range of cells involved in, for example, blood vessels, connective tissues, cranial nerve systems, immune systems and the like.

The designation "basic fibroblast growth factor" has been used commonly, because it has been found in 1974 as a fibroblast (3T3) growth factor having an isoelectric point (pI) of 9.6, though it has several other synonyms.

On the other hand, a protein having similar structure (140 amino acid residues) to bFGF but different pI (5.6) has been isolated in 1979 as a factor which enhances growth of myoblasts, and is now called acidic fibroblast growth factor (hereinafter referred to as "aFGF").

Since aFGF and bFGF bind to the same cell surface receptor, these two factors seem to have a similar reaction mechanism. These factors also have a similar tissue distribution though their contents are different.

A strong affinity for heparin (Kd, about $10^{-7}$M) is a noteworthy property common to aFGF and bFGF. It is known that these two factors also bind strongly to the sugar chain moiety of heparan sulfate proteoglycan in the extracellular tissue matrix or in the basement membrane, thus forming a non-diffusible storage state.

Both aFGF and bFGF are sensitive to (apt to be hydrolyzed by) proteases secreted from their producer cells or adjoining cells, but they show strong resistances against these enzymes once they are bound to heparin or heparan sulfate proteoglycan.

Based on these facts, their binding to heparan sulfate proteoglycan in the cell matrix can be regarded as a phenomenon essential for the accumulation and storage of these factors and for the effective exhibition of their functions when required. However, it is not known yet about the mechanism that the matrix-bound, non-diffusible and preservable growth factors are converted into diffusible and functional forms.

The aFGF and bFGF are now frequently used in cytological experiments in the form of reagents as markedly effective tissue growth factors. Also, because of their applicability as clinical drugs useful for blood vessel construction, tissue repairing, blood cell increment and the like, many test results have been reported.

The administration of these factors as clinical drugs is problematic because they are readily hydrolyzed by proteases and their dispersibility is low.

In the case of administering these factors as clinical drugs, it is problems that they are readily hydrolyzed by In order to overcome such problems, the use of these factors in the presence of heparin has been reported and the efficiency of such a means has been confirmed. However, application of heparin as a pharmaceutical drug is limited because of its strong anti-blood coagulation activity and occasional bleeding tendency.

JP-A-2-40399 discloses a complex consisting of glycosaminoglycan and a fibroblast growth factor mutein (hereinafter referred to as "FGF mutein") which is obtained by replacing certain amino acids of human bFGF with other amino acids, as well as a composition containing the FGF mutein and glycosaminoglycan (the term "JP-A" as used herein means an "unexamined published Japanese patent application"). This publication describes that the invention was accomplished based on a finding that stability of the FGF mutein increases markedly when glycosaminoglycan such as heparan sulfate and low molecular weight heparan sulfates prepared using hydrogen peroxide is added to an aqueous solution of the FGF mutein.

In addition, JP-A-63-66192 (hereinafter referred to as "Sanofi application") illustrates an invention entitled "Heparin-based Oligosaccharides having Affinity for Cell Growth Factors". The above invention aims at providing heparin type or heparan sulfate type oligosaccharides having markedly high affinities for heparin-binding cell growth factors, which can be obtained, for example, by a process which comprises the steps of: subjecting natural heparin or natural heparan sulfate chain which serves as a starting material to depolymerization (molecular weight reduction) with nitric acid, heparinase, heparitinase or periodic acid; subjecting the resulting product to alcohol precipitation for separating a fraction of saccharides having 10 monosaccharide residues or less and a fraction of saccharides having more than 10 monosaccharide residues; applying the fraction of saccharides having 10 monosaccharide residues or less to an agarose-acrylamide column for separating into a disaccharide fraction, a tetrasaccharide fraction, a hexasaccharide fraction, an octasaccharide fraction and a decasaccharide fraction; and removing chains having no affinity or medium affinity for FGF by FGF anion-Sepharose to obtain a fragment (oligosaccharide) consisting of hexasaccharides, octasaccharides, decasaccharides, dodecasaccharides with chemically modified chain ends when required, or of saccharides having at most 14 monosaccharide residues.

The Sanofi application also discloses that the fragment includes a product substantially comprising a chain having a specific affinity for a cationic or an anionic cell growth factor which recognizes heparin and pharmacologically acceptable salts thereof, wherein said chain comprises repetition of a structural unit represented by the following formula (I):

$$-(G-H)_n-G- \text{ or } -H-(G-H)_n \qquad (I)$$

wherein n represents an integer of from 2 to 6 and G—H corresponds to a disaccharide chain structure of (iduronic acid 2-O-sulfate)-(D-glucosamine-NH-sulfate 6-O-sulfate), G is a structural unit of L-iduronic acid 2-O-sulfate and H is a structural unit of D-glucosamine-NH-sulfate 6-O-sulfate.

Thus, a complex of the FGF mutein with glycosaminoglycan according to the Sanofi application is composed of the FGF mutein which is not a naturally occurring fibroblast growth factor, because certain amino acids of human basic fibroblast growth factor are replaced with other amino acids. In addition, though it discloses a low molecular weight heparan sulfate as an example of glycosaminoglycan, its illustrative description includes only a complex which consists of the FGF mutein and a relatively long-chained heparin or heparan sulfate. Such a complex possibly might have pharmacologically and physiologically unnecessary or improper structural moieties which react, for example, with antithrombin III, heparin cofactor II, platelet factor 4 and the like.

Also, the oligosaccharide according to the Sanofi application contains [iduronic acid 2-sulfate (α1→4)-glucosamine-NH-sulfate 6-O-sulfate]$_{2-6}$ as the structural unit in which all of the 6-position of glucosamine residues are sulfated and the oligosaccharide does not contain D-glucuronic acid, N-acetylglucosamine and L-iduronic acid. Thus, the oligosaccharide binds to FGF strongly depending on ionic nature and in other words, it does not physiologically or specifically bind to FGF, which means that it binds to other proteins and peptides and its binding activity to FGF might be possibly neutralized. Further, this heparin-derived oligosaccharide might possibly show improper pharmacological and physiological activities which are inherent to heparin.

SUMMARY OF THE INVENTION

Under these circumstances, the present inventors conducted intensive studies on saccharides having an affinity for FGF and found that some fractions derived from heparan sulfate have no affinity for FGF, while some fractions have an affinity for FGF, and as a consequence, succeeded in preparing oligosaccharides having an affinity for FGF from a fraction of heparan sulfate which binds to FGF.

An object of the present invention is to provide an oligosaccharide having an affinity for fibroblast growth factor which is composed of 8 to 18 monosaccharide residues wherein a principal disaccharide unit comprising L-iduronic acid 2-sulfate and N-sulfo-D-glucosamine.

Another object of the present invention is to provide a process for producing the oligosaccharide, which comprises the steps of: digesting heparan sulfate with Heparitinase I; allowing the resulting digest to bind to an acidic or basic fibroblast growth factor-bound carrier in the presence of chondroitin sulfate; and desorbing the bound digest from said carrier.

DETAILED DESCRIPTION OF THE INVENTION

Figure 1:
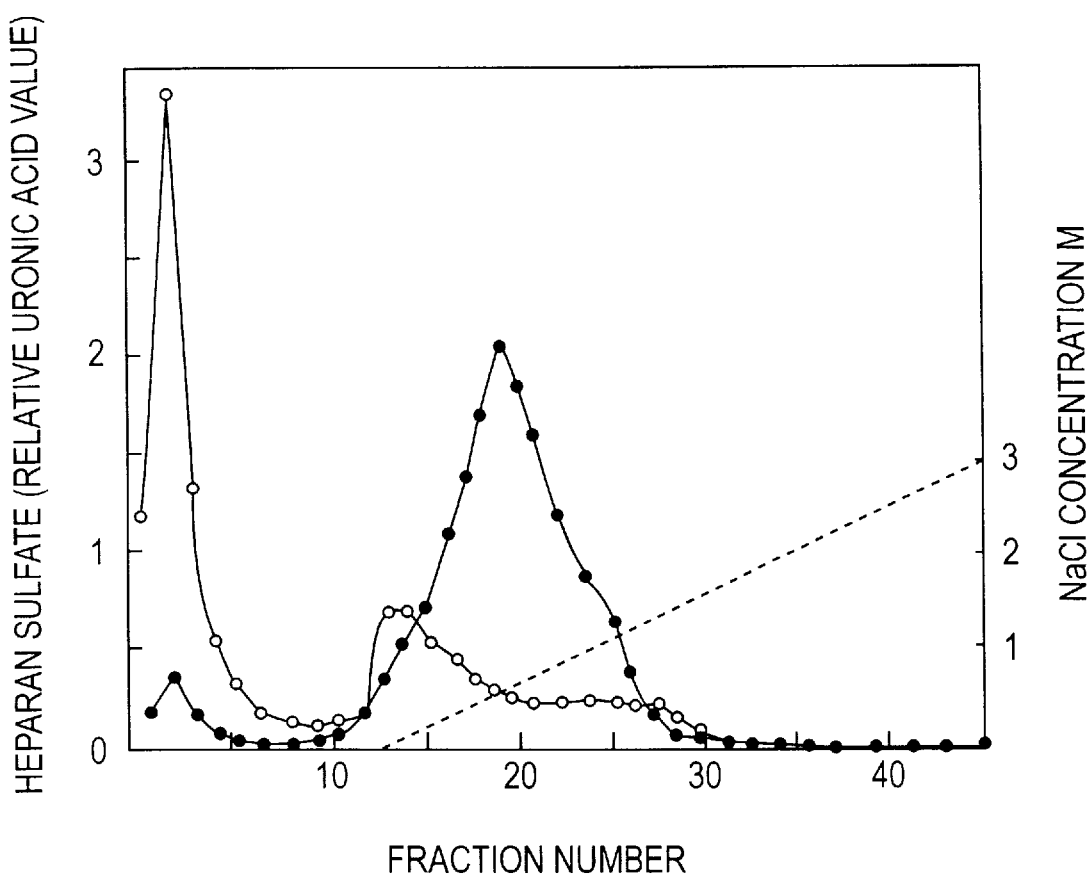
FIG. 1 shows elution patterns (from bFGF-Sepharose column) of heparan sulfate samples having high affinities for bFGF, where ● is a heparan sulfate of bovine aorta origin and ○ is a heparan sulfate of mouse EHS tumor origin.

The term "principal disaccharide unit" of the oligosaccharide as used herein means that the oligosaccharide contains the disaccharide as an essential unit in relatively large numbers, but not necessarily occupying most of the oligosaccharide chain.

Heparan sulfate as the starting material can be prepared in a conventional manner from, for example, viscera of fishes (salmon, mackerel and the like), tissues and viscera of birds (domestic fowl, quail and the like), tissues and viscera of mammals (cattle, swine, sheep and the like) and transplanted tumor tissues of experimental animals (rat, mouse, guinea pig and the like). From the view point of yield, activity and production cost, it is preferably to use the small intestines or the aorta of cattle, swine or sheep, cockscombs of domestic fowl and a crude heparan sulfate fraction obtained as a by-product in the process of heparin mass production.

When heparan sulfate is prepared from the above-described starting materials, it is necessary to remove heparin thoroughly and to avoid contamination of analogous polysaccharide components such as dermatan sulfate, chondroitin sulfate, hyaluronic acid, keratan sulfate and the like, which may be effected by selecting a proper combination of purification methods such as defatting of tissues, β-elimination in heparan sulfate and a core protein with sodium hydroxide, protein elimination with proteases, ethanol precipitation, cetyl pyridinium precipitation, precipitation removal of dermatan sulfate with Benedict's reagent, column chromatography using an anionic ion exchanger (DEAE cellulose for instance) and other proper techniques. Further, in order to remove such contaminating components, the digestion and molecular weight reduction may be carried out using proper hydrolases specific to contaminating polysaccharides to the extent that the oligosaccharide having an affinity for FGF according to the present invention can remain.

The heparan sulfate thus prepared is white powder, dissolves well in water, has an $[a]_D$ value of from +30 to +80 (varying depending on the materials used) and has a molar ratio of total hexosamine (all D-glucosamine) to total hexuronic acid (30 to 90% D-glucuronic acid and 10 to 70% L-iduronic acid, varying depending on the materials used) of about 1. In the heparan sulfate, molar ratios among N-acetyl, N-sulfuric acid and O-sulfuric acid groups vary fairly greatly.

Preparation of heparan sulfate suitable for use as a material of the present invention is described in detail below.

The heparan sulfate obtained above is dissolved in a buffer containing chondroitin sulfate and incubated together with an aFGF- or bFGF-bound carrier, thereby binding the heparan sulfate suitable as the material of the present invention to said carrier. After removing unbound heparan sulfate and other impurities, the heparan sulfate portion useful as the material of the present invention is desorbed from the carrier using a buffer containing sodium chloride.

Examples of the carrier to which FGF is bound include agarose gel and the like, preferably Sephadex (available from Pharmacia), Biogel (available from Bio-Rad Laboratories), Sepharose (available from Pharmacia) and the like.

The FGF to be bound to the carrier may be either aFGF or bFGF (in some cases, aFGF or bFGF is hereinafter described simply as FGF). Both aFGF and bFGF are commercially available, for example, natural aFGF (isolated from bovine pituitary glands, Genzyme), human recombinant aFGF (Amersham) and bovine recombinant bFGF (Amersham).

The bFGF-bound carrier (hereinafter referred to as bFGF carrier) may be prepared for example in the following manner.

An appropriate amount of bFGF is dissolved in an appropriate volume of a coupling buffer and heparan sulfate previously treated with acetic anhydride is added thereto. For example, 200 µg of bFGF is dissolved in 500 µl of a coupling buffer (0.4M NaCl in 0.1M NaHCO$_3$, pH 8.3) and 200 µg of acetylated heparan sulfate is added thereto. Heparan sulfate can be acetylated by dissolving 200 µg of heparan sulfate in 1 ml of a saturated NaHCO$_3$ solution, adding an equivalent volume of 5% acetic anhydride thereto, allowing the mixture to stand at room temperature for 10 minutes, and then 2-fold volume of 95% ethanol containing 1% (w/w) of potassium acetate to obtain acetylated heparan sulfate as a precipitate. Separately, an agarose gel (Sepharose for instance) activated in advance with cyanogen bromide (CNBr) is suspended in a coupling buffer and added to the above solution. A CNBr-activated agarose gel which is commercially available, for example, CNBr-activated Sepharose 4B (Pharmacia), is suspended in the above-described coupling buffer to give a concentration of 50% (v/v). To a 1 ml portion of the resulting suspension is added the mixture of acetylated heparan sulfate and bFGF. The reaction is carried out overnight, at a low temperature, for example, 4° C. with shaking. The gel is collected by filtration and suspended in 0.1M Tris-HCl buffer (pH 8.0). The suspension is allowed to react overnight at 4° C. with shaking followed by thorough washing with the coupling buffer to obtain the bFGF carrier.

The aFGF-bound carrier can be prepared in the same manner as described above except that the procedure is carried out in the presence of 5 mM dithiothreitol which is a stabilizer for aFGF.

Binding of the heparan sulfate to the FGF carrier and subsequent desorption from the carrier may be effected by a batch process in which the FGF carrier equilibrated with a specific solution is allowed to contact with the heparan sulfate dissolved in the specific solution, and the heparan sulfate thus bound to the FGF carrier is desorbed using a specific eluent.

It may be effected also by column chromatography in which the FGF carrier is packed in a column, the packed carrier is equilibrated with a specific solution, the heparan sulfate dissolved in the specific solution is passed through the column to bind it to the FGF carrier and then the thus bound heparan sulfate is eluted from the carrier with a specific eluent to collect a fraction corresponding to a fraction containing the desired oligosaccharides as shown in a calibration curve which has been prepared in advance by using a $^3$H-labeled standard substance or by determining uronic acid content of the standard substance. The standard substance is the heparan sulfate fraction which binds the FGF carrier and the constituent sugar of the fraction is determined by the carbazole-sulfuric acid method and the orcinol-sulfuric acid method. In the case of using a $^3$H-labeled standard substance, the heparan sulfate fraction is digested with an enzyme such as Hepatirinase I and the thus-obtained oligosaccharides are labeled with [$^3$H]NaBH$_4$ and applied to the FGF carrier to prepare the calibration curve.

A phosphate buffer containing at least one of chondroitin sulfate selected from chondroitin sulfate A, chondroitin sulfate B, chondroitin sulfate C, chondroitin sulfate D and chondroitin sulfate E may be used preferably as a specific solution for equilibrating the FGF carrier and dissolving heparan sulfate. Such chondroitin sulfate is commercially available, for example, chondroitin 6-sulfate (from shark cartilage, Sekagaku Corporation). A concentration of chondroitin sulfate is adjusted to about 200 µg/ml. Usable as a phosphate buffer is phosphate-buffered saline (PBS) (+) (pH 7.2) containing 0.15M NaCl.

A phosphate buffer containing sodium chloride may be used preferably as a specific eluent. A concentration of sodium chloride may varied within the range of from 0 to 3M. A PBS (+) is used as a phosphate buffer.

Elution of the heparan sulfate from the column with the specific eluent may be effected, for example, using a phosphate buffer such as PBS(+) (pH 7.2) containing 2M NaCl or by a linear concentration gradient technique in which concentration of sodium chloride in a phosphate buffer such as PBS(+) (pH 7.2) is increased gradually, for example, 0 to 3M.

In the case of the aFGF carrier, 5 mM dithiothreitol is contained in the phosphate buffer.

The preparation of heparan sulfate described above is effective for the collection of heparan sulfate having a high affinity for the FGF carrier from a heparan sulfate material which contains such a heparan sulfate in a moderate or low concentration.

Examples of materials containing a large amount of heparan sulfate having an affinity for the FGF carrier include one derived from swine aortas (about 92%) and the like, and those with a moderate or low concentration include one derived from mouse EHS tumor (about 46%) and the like.

The aforementioned preparation method may be omitted when a material to be used is abundant in a heparan sulfate having an affinity for the FGF carrier, such as a heparan sulfate material of swine aorta origin.

Preparation of an oligosaccharide having an affinity for FGF, which comprises 8 to 18 monosaccharide residues with its principal disaccharide unit comprising L-iduronic acid 2-sulfate and N-sulfo-D-glucosamine is described below.

A mixture containing the oligosaccharides of the present invention can be prepared by subjecting the thus prepared heparan sulfate having an affinity for the FGF carrier to digestion with Heparitinase I under usual conditions.

The term "Heparitinase I" as used herein means enzymes such as Heparitinase I (available from Seikagaku Corporation) and Heparitinase III (available from Sigma Chemical Co.), which belong to the enzymes classified as EC 4.2.2.8. These enzymes do not digest bonds related to L-iduronic acid 2-sulfate residue, such as a bond between L-iduronic acid and N-sulfo-D-glucosamine, a bond between L-iduronic acid and N-sulfo-D-glucosamine glucosamine 6-sulfate, a bond between L-iduronic acid 2-sulfate and N-sulfo-D-glucosamine and a bond between L-iduronic acid 2-sulfate and N-sulfo-D-glucosamine 6-sulfate.

The digestion reaction can be carried out by adding about 5 mg of the heparan sulfate having an affinity for FGF to about 500 µl of 0.05M Tris-HCl buffer (pH 7.2) containing 25–200 mU of Heparitinase I (EC 4.2.2.8, Sekagaku Corporation), about 0.5 µmol of CaCl$_2$ and about 50 µg of bovine serum albumin and incubating the mixture at 30°–37° C. for about 1 hour.

The thus obtained oligosaccharides are dissolved in the specific solution used in the above-mentioned preparation of the FGF carrier and then allowed to contact with the FGF carrier so as to bind the oligosaccharides thoroughly to the carrier at a low temperature. After washing with the specific solution to remove unbound oligosaccharides, the oligosaccharides of the present invention having an affinity for the FGF carrier is desorbed from the carrier using the aforementioned eluent. This procedure can be carried out in the same manner as described above.

A phosphate buffer containing at least one of chondroitin sulfate selected from chondroitin sulfate A, chondroitin sulfate B, chondroitin sulfate C, chondroitin sulfate D and chondroitin sulfate E may be used preferably as the specific solution for dissolving the oligosaccharides, and a phosphate buffer containing sodium chloride may be used preferably as the specific eluent.

Binding of the oligosaccharide to the FGF carrier and subsequent desorption may be effected by a batch process in which the FGF carrier equilibrated with a specific solution is allowed to contact with the oligosaccharide dissolved in the specific solution, and the oligosaccharide thus bound to the FGF carrier is desorbed using a specific eluent.

It may be effected also by column chromatography in which the FGF carrier is packed in a column, the packed carrier is equilibrated with the specific solution, the oligosaccharide dissolved in the specific solution is passed through the column to bind it to the FGF carrier and then the thus bound oligosaccharide is eluted from the carrier with the specific eluent to collect a fraction corresponding to a position calibrated in advance with a standard substance (for example, using a $^3$H-labeled sample).

Elution of the oligosaccharide from the column with the specific eluent may be effected, for example, by a linear concentration gradient technique in which concentration of sodium chloride in a phosphate buffer is increased gradually.

The thus obtained oligosaccharide has an affinity for the FGF carrier and is composed of 8 to 18 monosaccharide residues with its principal disaccharide unit comprising L-iduronic acid 2-sulfate and N-sulfo-D-glucosamine.

The oligosaccharide of the present invention may be in the form of a mixture of two or more of the above-described 8 to 18 monosaccharide residues.

The oligosaccharide of the present invention composed of 8 to 18 monosaccharide residues may be further fractionated into specific saccharide sizes, for example, in terms of molecular weights.

Molecular sieve chromatography may be used for this purpose. In that instance, agarose gel or the like may be used as a packing agent or a carrier. Preferred examples of the carrier include Sephadex (available from Pharmacia), Biogel (available from Bio-Rad Laboratories), Sepharose (available from Pharmacia) and the like. For example, each of di- to octadecasaccharides may be isolated by a column chromatography using a column packed with Sephadex G-50 (available from Pharmacia).

The oligosaccharide having an affinity for FGF according to the present invention is produced from heparan sulfate which is stored in extracellular matrices in vivo and known as a component of a compound to which physiologically active FGF is bound. The process for producing the oligosaccharide of the present invention is based on three important factors that: (1) heparan sulfate is digested with Heparitinase I so that it retains FGF-binding domain, (2) bFGF-fixed column is prepared under such conditions that the heparan sulfate binding domain can be protected and (3) affinity chromatography prevents non-specific ion binding.

The oligosaccharide of the present invention has an affinity for FGF but does not react with antithrombin III, heparin cofactor II, platelet factor 4 and the like, which is composed of 8 to 18 monosaccharide residues with its principal disaccharide unit comprising L-iduronic acid 2-sulfate and N-sulfo-D-glucosamine. The oligosaccharide of the present invention can easily form a complex with FGF when only they are mixed together. The composition comprising FGF and the oligosaccharide of the present invention is expected to be useful as a drug.

The following examples are provided to further illustrate the present invention, but are not construed to limit the scope of the invention.

EXAMPLE

Preparation of bFGF-Sepharose

A 200 μg portion of bFGF (a bovine-derived recombination product, available from Amersham) was dissolved in 0.5 ml of a coupling buffer (0.1M NaHCO$_3$ containing 0.4M NaCl, pH 8.3). To the resulting solution was added 200 μg of heparan sulfate (prepared from swine aortas) which had been treated with acetic anhydride in advance. The mixture was allowed to stand at room temperature for 10 minutes.

A 0.5 ml portion of Sepharose (available from Pharmacia) which had been activated with cyanogen bromide (CNBr) was suspended in the same volume of the coupling buffer, and the bFGF solution prepared above was added thereto. The resulting mixture was gently shaken overnight at 4° C.

The gel thus obtained was washed thoroughly with the coupling buffer and suspended in 900 μl of Tris-HCl buffer (0.1M, pH 8.0), and the resulting suspension was gently shaken overnight at 4° C. to prepare bFGF-Sepharose (bound bFGF amount, 120 μg).

Preparation of Standard Heparan Sulfate Elution Curve Using bFGF-Sepharose

Heparan sulfate was treated with [$^3$H] NaBH$_4$ to label the reducing end of heparan sulfate with $^3$H. The thus labeled heparan sulfate was subjected to chromatography using a column packed with the bFGF-Sepharose, and the eluates were monitored by radiation measurement of $^3$H to prepare a standard elution curve.

Fractionation of Heparan Sulfate Having High Affinity for bFGF

Buffer A* was prepared by dissolving chondroitin sulfate (shark origin, available from Seikagaku Corporation) to a final concentration of 0.02% by weight in a 0.1M phosphate buffer containing 0.9 mM of CaCl$_2$ and 0.48 mM of MgCl$_2$ (PBS, pH 7.2).

A 100 μg portion of swine aortas-derived heparan sulfate was dissolved in three volumes of buffer A* and applied to a bFGF-Sepharose column (bound bFGF amount, 120 μg) which had been equilibrated with buffer A*, and the resulting column was gently shaken at 4° C. for 2 hours.

The column was washed with buffer A* to remove heparan sulfate which did not bind to the gel and then subjected to a linear concentration gradient elution with PBS/3M NaCl. After digestion with chondroitinase, the hexuronic acid value of chondroitinase-resistant substances in the eluate was measured according to an elution curve which had been prepared by monitoring $^3$H radiation of a standard sample, thereby preparing an elution curve shown in FIG. 1 and fractionating a heparan sulfate portion having a high affinity for bFGF.

Another heparan sulfate fraction having a high affinity for bFGF was obtained by treating mouse EHS tumor heparan sulfate in the same manner as described above. The results are also shown in FIG. 1.

About 92% of the swine aortas-derived heparan sulfate was bound to the bFGF-Sepharose, while only about 46% of the mouse EHS tumor heparan sulfate was bound thereto.

Preparation of Oligosaccharide Having Affinity for bFGF

The thus obtained heparan sulfate fraction having a high affinity for bFGF was treated in the following manner to prepare a mixture of oligosaccharides.

A 50 milli-unit portion of Heparitinase I (EC 4.2.2.8, available from Seikagaku Corporation), 25 μmol of Tris-HCl buffer (pH 7.2), 0.5 μmol of CaCl$_2$ and 50 μg of bovine serum albumin were made into a 500 μl solution. To this was added 5 mg of the heparan sulfate fraction having a high affinity for bFGF, and the resulting mixture was incubated at 37° C. for 60 minutes to prepare a mixture of oligosaccharides. The reaction was terminated by heating at 100° C. for 2 minutes.

Figure 2:
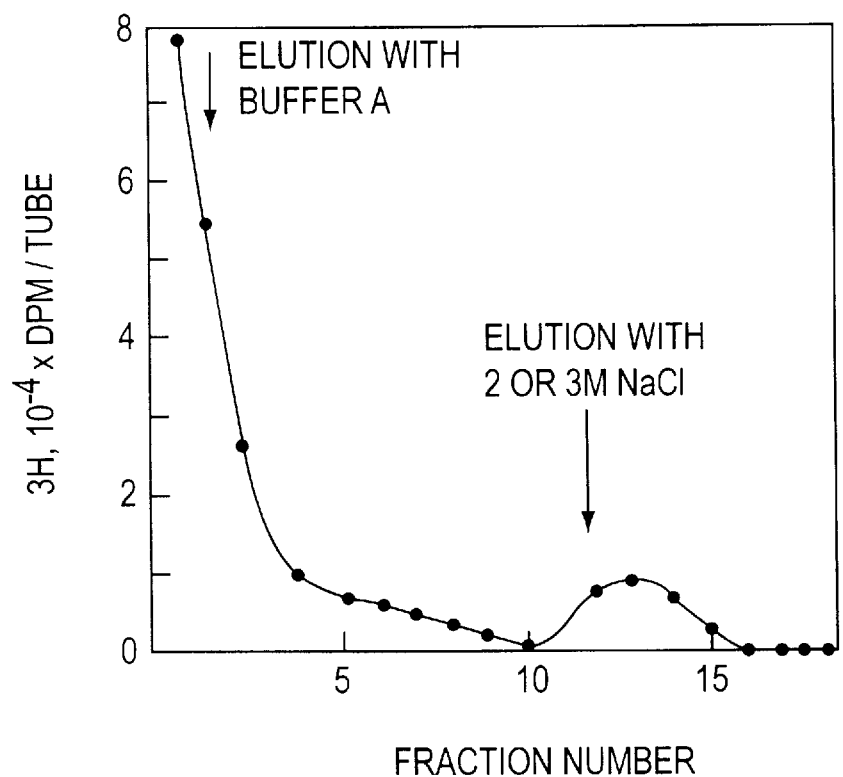
FIG. 2 shows an elution pattern (from bFGF-Sepharose column) of an oligosaccharide sample having an affinity for bFGF.

A 50 μg portion of the thus obtained oligosaccharide mixture was dissolved in 300 μl of the aforementioned buffer A*, and the solution was applied to a bFGF-Sepharose column which had been calibrated in advance with a standard sample. After shaking at 4° C. for 2 hours, oligosaccharide portions which did not bind to the carrier were removed by washing with 5 ml of the buffer A*, and elution was carried out with PBS buffer containing 3M NaCl. Using a $^3$H-labeled sample, an elution curve shown in FIG. 2 was prepared.

Among the oligosaccharides originated from swine aorta heparan sulfate, about 13% were found to be the desired oligosaccharide having an affinity for FGF.

Purification of oligosaccharide having affinity for bFGF

The thus obtained oligosaccharide fraction was further purified by applying it to a column (1.2×120 cm) packed with Sephadex G-50 (available from Pharmacia) and eluting with 0.5M NaCl.

Figure 3:
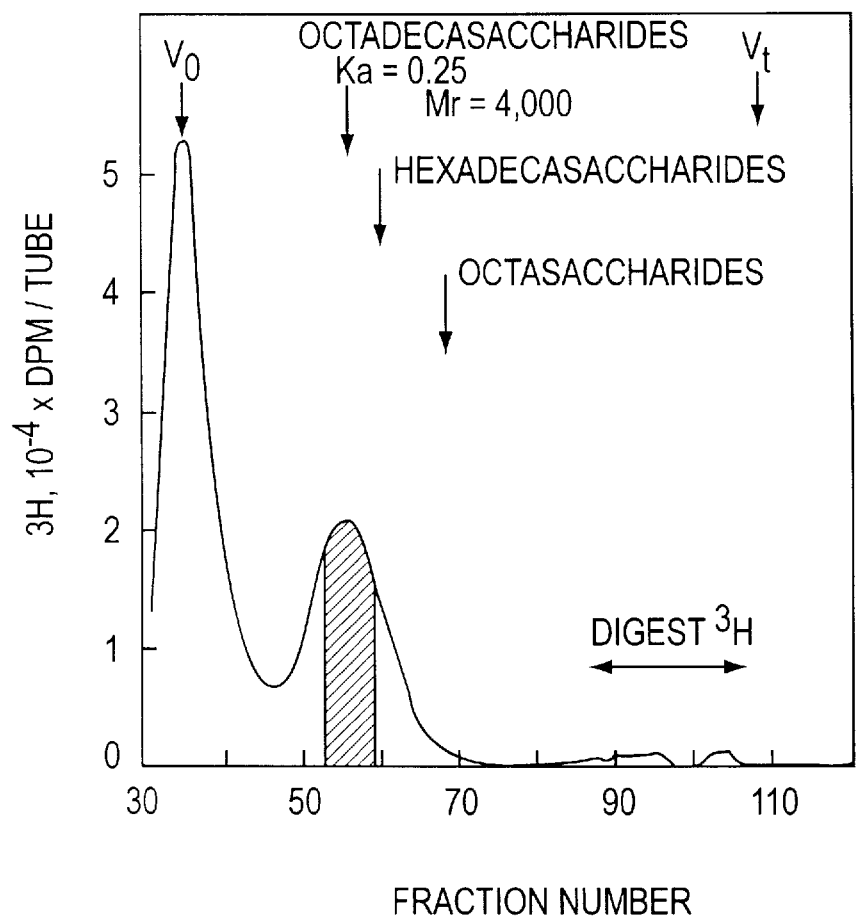
FIG. 3 shows an elution pattern (from Sephadex G-50) of an oligosaccharide sample having an affinity for FGF.

An elution curve was prepared in advance by using a $^3$H-labeled standard sample. As shown in FIG. 3, a broad elution pattern was obtained with a peak which corresponds to hexadeca- to octadecasaccharides (average monosaccharide residues: 16).

The thus obtained fraction of hexadeca- to octadecasaccharides (hereinafter referred to as hexadecasaccharide fraction) was digested into disaccharides under the following conditions.

A 4 milli-unit portion of Heparitinase I, 2 milli-units of Heparitinase II, 4 milli-units of Heparinase (EC 4.2.2.7, available from Seikagaku Corporation), 50 mM of Tris-HCl buffer (pH 7.2, final concentration), 1 mM of CaCl$_2$ (final concentration) and 2.5 µg of bovine serum albumin were made into a 25 µl aqueous solution with water. To this was added 10 µg of the above-obtained hexadecasaccharide fraction and the resulting mixture was incubated at 37° C. for 2 hours to digest the component into disaccharides. The reaction was terminated by heating at 100° C. for 2 minutes. Composition of the digest is shown in Table 1 in which disaccharide components of oligosaccharides (hexadecasaccharide fraction) which did not bind to the bFGF-Sepharose column when the same starting material was treated by the same procedure are also shown.

TABLE 1

| | Mole/8 × disaccharide unit | |
|---|---|---|
| Disaccharide unit[1] | Oligosaccharides of the invention[2] | Oligosaccharides which do not bind to FGF carrier[3] |
| GlcA-GlcNAc | 2 | 3.3 |
| GlcA-GlcNAc(6S) | 0.65 | 1.1 |
| GlcA-GlcNS | 1 | 2 |
| GlcA-GlcNS(6S) | 0.35 | 0.4 |
| IdoA(2S)-GlcNS | 3 | 0.4 |
| IdoA(2S)-GlcNS(6S) | 1 | 0.8 |
| Not identified | ≦0.02 | ≦0.02 |

[1]GlcA, D-glucuronic acid; IdoA(2S), L-iduronic acid 2-sulfate; GlcNAc, N-acetyl-D-glucosamine; GlcNAc(6S), N-acetyl-D-glucosamine 6-sulfate; GlcNS, N-sulfo-D-glucosamine; GlcNS(6S), N-sulfo-D-glucosamine 6-sulfate Glycoside linkage type in oligosaccharides: β-1,4 D-glucuronosyl linkage; α-1,4 L-iduronosyl linkage; N-acetyl (and N-sulfo)-D-glucosaminyl linkage
[2]The hexadecasaccharide fraction prepared in the above example having an affinity for bFGF
[3]Oligosaccharides (hexadecasaccharide fraction) which did not bind to the bFGF-Sepharose in the above example Physiological Activity of Oligosaccharide Having Affinity for FGF (1) Addition of protease resistance 90 µl of Tris-HCl buffer (0.025M, pH 7.0) containing 20 µg of the oligosaccharide (hexadecasaccharide fraction) having an affinity for FGF according to the present invention, a varied amount (10, 20, 30 or 40 ng) of aFGF, 50 µg of bovine serum albumin, 0.15M of NaCl, 0.9 mM of CaCl$_2$ and 0.4 mM of MgCl$_2$ was incubated at 37° C. for 5 minutes. To this was added 10 µl (0.65 unit) of Trypsin-Sepharose (available from Sigma), and the mixture was incubated at 37° C. for 3 hours. The resulting mixture was subjected to centrifugation to remove the Trypsin-Sepharose, and the resulting filtrate (supernatant) was added to a culture system of bovine aorta smooth tissues to measure an effect of the oligosaccharide on the incorporation of [$^3$H] thymidine into DNA, with the results shown in FIG. 4. Also showed in the figure are results obtained in the case that 20 µg of oligosaccharides (hexadecasaccharide fraction) which did not bind to the bFGF-Sepharose were used and oligosaccharides are not used.

Figure 4:
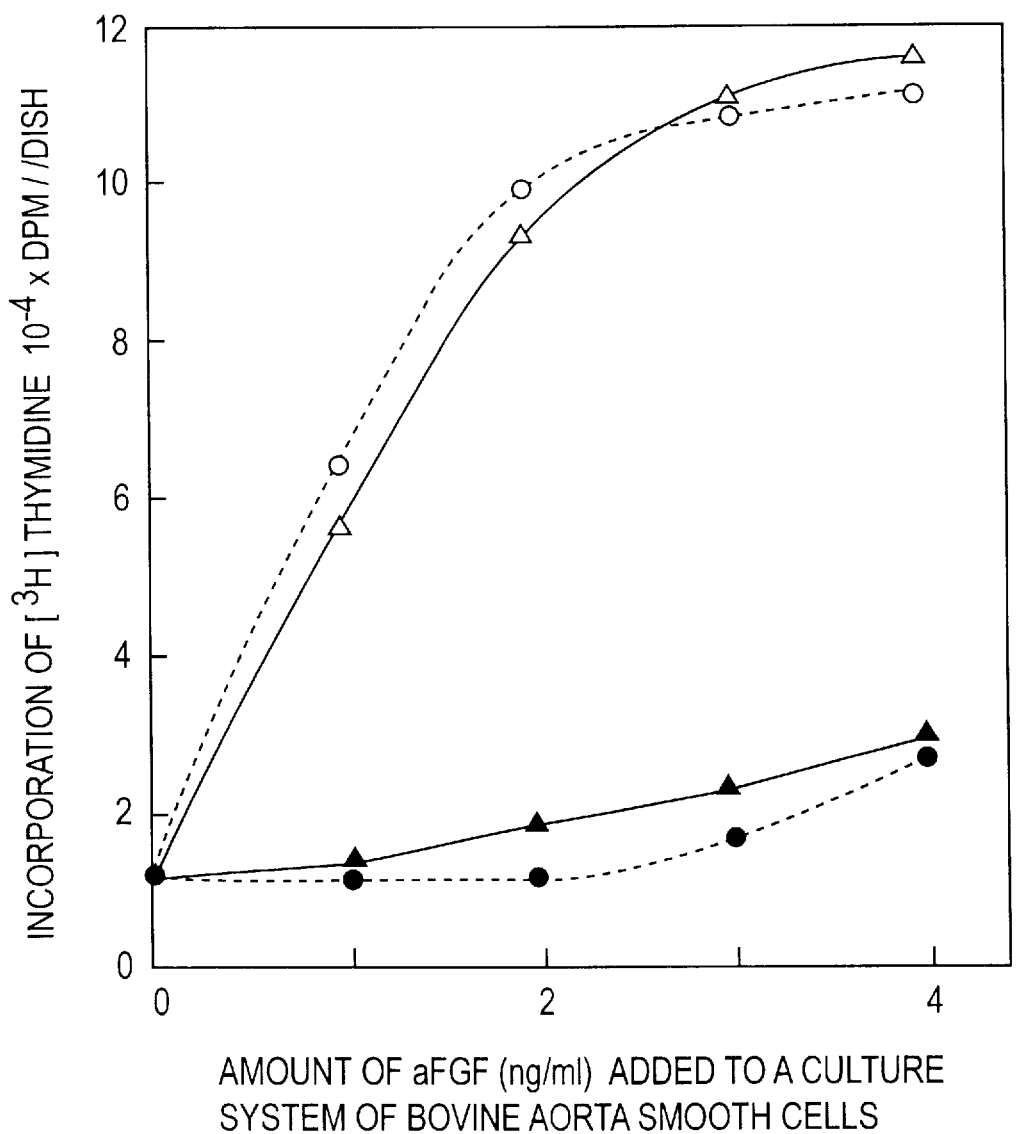
FIG. 4 is a graph showing an effect of an oligosaccharide sample having an affinity for FGF on the incorporation of [$^3$H]thymidine into DNA, where ○ is aFGF, ● is aFGF plus trypsin treatment, Δ is aFGF plus an oligosaccharide having an affinity for FGF plus trypsin treatment and ▲ is aFGF plus an oligosaccharide having no affinity for FGF plus trypsin treatment.

As shown in FIG. 4, it is found that the oligosaccharide of the present invention having an affinity for FGF provided almost perfect protection against inactivation of aFGF under the conditions that the aFGF was completely inactivated. It is also evident from FIG. 4 that the oligosaccharides (hexadecasaccharide fraction) which did not bind to the bFGF-Sepharose have no effect to protect FGF from its inactivation.

(2) Improvement of intra-matrix dispersion

Bovine endothelial cells were cultured on tissue culture dishes having a diameter of 60 mm to obtain monolayer (confluent stage) cells. A 12 mm-diameter bottom-less cup was set on the center of the monolayer in each culture dish, and 200 µl of MEM medium containing 15 ng of bFGF alone or 15 ng of bFGF and 20 µg of the above-obtained oligosaccharides of the present invention was poured in the cup. After 36 hours of culturing under usual conditions, the cell layer was washed with PBS, fixed with methanol and then subjected to Giemsa staining to observe changes in the cell morphology under a light microscope.

Cells stimulated by bFGF showed remarkable growth and these cells were clearly distinguishable from the control cells. It can be estimated that bFGF was diffused to the extent of only within a diameter of 4 to 5 mm around the cup in the case that bFGF alone was added, while bFGF was diffused to the entire area in the 60 mm culture dish in the case that bFGF and the oligosaccharides of the present invention were added together.

Thus, it is apparent that, when FGF is used with the oligosaccharides of the present invention, FGF shows strong resistances against proteases derived from animal cells and tissues, such as plasmin, trypsin and the like, and has high dispersability in extracellular matrix as compared to the case that aFGF or bFGF is used alone. The composition containing FGF and the oligosaccarhides of the present invention is expected to be useful as a pharmaceutical drug.

While the invention has been described in detail and with reference to specific embodiments thereof, it will be apparent to one skilled in the art that various changes and modifications can be made therein without departing from the spirit and scope thereof.

What is claimed is:

1. An oligosaccharide with affinity for fibroblast growth factor (FGF) and no reactivity with antithrombin III and heparin cofactor II, and which enhances dispersion of fibroblast growth factor in an extracellular matrix, wherein said oligosaccharide has 16 to 18 monosaccharide residues, and contains at least one disaccharide unit composed of L-iduronic acid 2-sulfate and N-sulfo-D-glucosamine.

2. A method for improving dispersion of FGF in an extracellular matrix comprising combining FGF present in an extracellular matrix with an oligosaccharide as claimed in claim 1.

3. An oligosaccharide with affinity for fibroblast growth factor (FGF) and no reactivity with antithrombin III and heparin cofactor II, and which enhances dispersion of fibroblast growth factor in an extracellular matrix, wherein said oligosaccharide has 16 to 18 monosaccharide residues, and contains at least one disaccharide unit composed of L-iduronic acid 2-sulfate and N-sulfo-D-glucosamine and the molar ratio of said disaccharide unit and a disaccharide unit composed of L-iduronic acid 2-sulfate and N-sulfo-D-glucosamine 6-sulfate is 3:1.

4. A method for improving dispersion of FGF in an extracellular matrix comprising combining FGF present in an extracellular matrix with an oligosaccharide as claimed in claim 3.

5. An oligosaccharide with affinity for fibroblast growth factor (FGF) and no reactivity with antithrombin III and heparin cofactor II, and which enhances dispersion of fibroblast growth factor in an extracellular matrix, wherein said oligosaccharide is a degradation product of heparan sulfate using heparitinase I, has 16 to 18 monosaccharide residues, and contains at least one disaccharide unit composed of L-iduronic acid 2-sulfate and N-sulfo-D-glucosamine.

6. A method for improving dispersion of FGF in an extracellular matrix comprising combining FGF present in an extracellular matrix with oligosaccharides of claim 5.

7. An oligosaccharide with affinity for fibroblast growth factor (FGF) and no reactivity with antithrombin III and heparin cofactor II, and which enhances dispersion of fibroblast growth factor in an extracellular matrix, wherein said oligosaccharide is a degradation product of heparan sulfate using heparitinase I, has 16 to 18 monosaccharide residues, and contains at least one disaccharide unit composed of L-iduronic acid 2-sulfate and N-sulfo-D-glucosamine and wherein the molar ratio of said disaccharide unit and a disaccharide unit composed of L-iduronic acid 2-sulfate and N-sulfo-D-glucosamine 6-sulfate is 3:1.

8. A method for improving dispersion of FGF in an extracellular matrix comprising combining FGF present in an extracellular matrix with oligosaccharides of claim 7.

* * * * *